United States Patent
Ota et al.

(10) Patent No.: US 8,564,444 B2
(45) Date of Patent: Oct. 22, 2013

(54) MOBILE SANITIZING DEVICES AND SYSTEMS FOR DISPENSING SANITIZER SOLUTION

(75) Inventors: Yasuhiro Ota, Union, KY (US); Masaru Ryumae, Union, KY (US); Keiichi Sato, Chicago, IL (US); Shin Sano, Oak Park, IL (US)

(73) Assignees: Toyota Motor Engineering & Manufacturing North America, Inc., Erlanger, KY (US); Illinois Institute of Technology, Chicago, IL (US)

( * ) Notice: Subject to any disclaimer, the term of this patent is extended or adjusted under 35 U.S.C. 154(b) by 518 days.

(21) Appl. No.: 12/847,280

(22) Filed: Jul. 30, 2010

(65) Prior Publication Data

US 2012/0024890 A1 Feb. 2, 2012

(51) Int. Cl.
*G08B 23/00* (2006.01)

(52) U.S. Cl.
USPC ............ 340/573.1; 340/539.1; 340/618; 700/245; 901/1

(58) Field of Classification Search
USPC ............ 340/573.1, 539.1, 618; 901/1, 46, 50; 701/400, 537, 538
See application file for complete search history.

(56) References Cited

U.S. PATENT DOCUMENTS

| | | |
|---|---|---|
| 4,942,631 A | 7/1990 | Rosa |
| 4,999,929 A | 3/1991 | Dutton |
| 5,179,843 A | 1/1993 | Cohausz |
| 6,404,837 B1 | 6/2002 | Thompson et al. |
| 6,691,897 B2 | 2/2004 | Ashe |
| 6,707,873 B2 | 3/2004 | Thompson et al. |
| 6,883,563 B2 | 4/2005 | Smith |
| 7,082,350 B2 | 7/2006 | Skoog |
| 7,597,122 B1 | 10/2009 | Smith |
| 2008/0084175 A1 | 4/2008 | Hollis |
| 2008/0087719 A1 | 4/2008 | Sahud |
| 2008/0136649 A1 | 6/2008 | Van De Hey |
| 2008/0230285 A1 | 9/2008 | Bewley et al. |
| 2009/0115610 A1* | 5/2009 | Steinhage et al. ......... 340/572.1 |
| 2010/0256812 A1* | 10/2010 | Tsusaka et al. ............... 700/254 |
| 2011/0018412 A1* | 1/2011 | Swanek ................. 312/249.11 |

* cited by examiner

*Primary Examiner* — Thomas Mullen
(74) *Attorney, Agent, or Firm* — Dinsmore & Shohl LLP (57) ABSTRACT

A mobile sanitizing device may include a sanitizer solution dispenser module, a motorized wheel assembly, and a controller module. The sanitizer solution dispenser module may be operable to dispense the sanitizer solution. The motorized wheel includes at least one wheel and is coupled to the sanitizer solution dispenser module. The controller module includes a microcontroller and a memory, and is programmed to log a sanitization record into a sanitization history of at least one user, compare the sanitization history of the user with a sanitization standard, and control the motorized wheel assembly to cause the mobile sanitizing device to approach the user to dispense sanitizing solution to the user when the sanitization history does not meet the sanitization standard.

20 Claims, 6 Drawing Sheets

MOBILE SANITIZING DEVICES AND SYSTEMS FOR DISPENSING SANITIZER SOLUTION

TECHNICAL FIELD

The present specification generally relates to sanitizer devices for providing sanitizer solution to users and, more specifically, mobile sanitizing devices for autonomously approaching users to initiate a sanitizing session and provide sanitizer solution.

BACKGROUND

Viral and bacterial infections remain a great concern. With the wide spread problem of viruses such as the H1N1 flu virus epidemic, it has become even more important to prevent infection as much as possible. Although most infections could be prevented by thoroughly washing hands or rubbing hands with antiseptic sanitization gel, people often fail to perform hand sanitizing simply because of unavailability of the wash basin or sanitization gel when necessary. Additionally, people often forget to wash their hands or use sanitization gel.

Accordingly, a need exists for alternative sanitizing devices for autonomously approaching users to provide sanitizer solution when it is needed.

SUMMARY

In one embodiment, a mobile sanitizing device for dispensing sanitizer solution may include a sanitizer solution dispenser module, a motorized wheel assembly, and a controller module. The sanitizer solution dispenser module operable to dispense the sanitizer solution. The motorized wheel includes at least one wheel and is coupled to the sanitizer solution dispenser module. The controller module includes a microcontroller and a memory, and is programmed to log a sanitization record into a sanitization history of at least one user, wherein the sanitization history is stored in the memory, compare the sanitization history of the user with a sanitization standard, and control the mobile sanitizing device to approach the user to dispense sanitizing solution to the user when the sanitization history does not meet the sanitization standard.

In another embodiment, a mobile sanitizing device for dispensing a sanitizer solution may include a sanitizer solution dispenser module, a motorized wheel assembly, a balance control sensor and a controller module. The sanitizer solution dispenser may be operable to dispense the sanitizer solution. The motorized wheel assembly may include an omni-directional wheel that is coupled to the sanitizer solution dispenser module. The balance control sensor provides a balance signal corresponding to an orientation of the mobile sanitizing device. The controller module includes a microcontroller and a memory and is operable to receive the balance signal from the balance control sensor and provide a drive signal to the motorized wheel assembly in accordance with the balance signal and an inverted pendulum control algorithm such that the mobile sanitizing device remains in an upright position during an unsupported operation.

In yet another embodiment, a sanitization system may include a wireless communications network, a central server communicably coupled to wireless communications network and a mobile sanitizing device. The mobile sanitizing device may further include a sanitizer solution dispenser module operable to dispense a sanitizer solution, a motorized wheel assembly including at least one wheel, and a controller module. The motorized wheel assembly is coupled to the sanitizer solution dispenser module. The controller module may further include a microcontroller, a memory, and a wireless communications device communicably coupled to wireless communications network. The wireless communications device detects a location of the mobile sanitizing device and a location of a user and transmits proximity data over wireless communications network. The proximity data corresponds to the location of the mobile sanitizing device and the location of the user. The central server receives the proximity data over the wireless communications network, calculates a navigation route, and transmits navigation information to the wireless communications device over the wireless communications network in accordance with the navigation route. The controller module receives the navigation information from the central server and provides a drive signal to the motorized wheel assembly to cause the mobile sanitizing device to autonomously approach a user in need of sanitization.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, wherein like structure is indicated with like reference numerals and in which:

DETAILED DESCRIPTION

Figure 1:
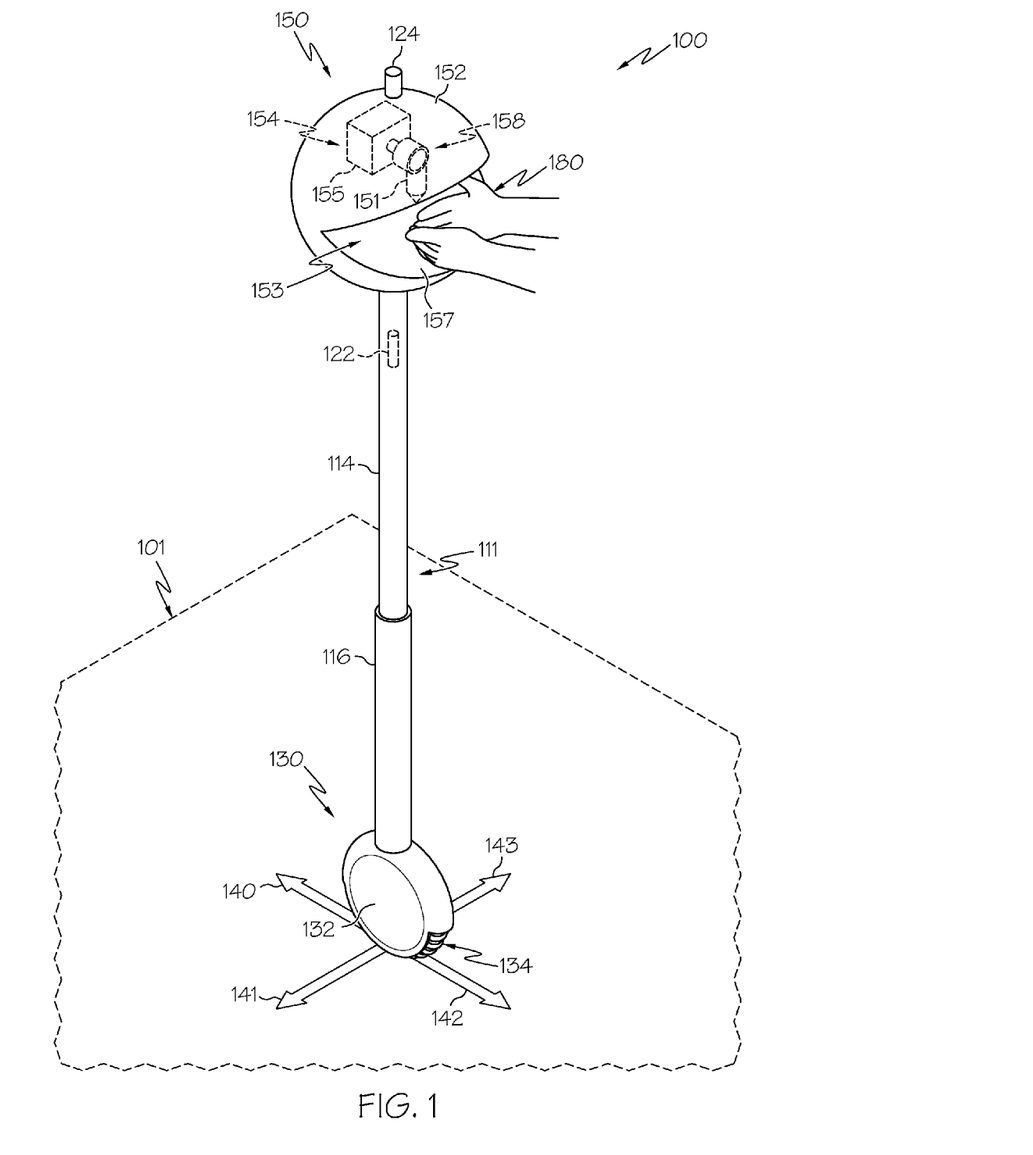
FIG. 1 depicts a mobile sanitizing device according to one or more embodiments shown and described herein.

FIG. 1 generally depicts one embodiment of a mobile sanitizing device for dispensing sanitizer solution. The mobile sanitizing device generally comprises a sanitizer solution dispenser module, a motorized wheel assembly coupled to the sanitizer solution dispenser module, and a controller. The sanitizer solution dispenser module may further comprise a sanitizer solution reservoir and a dispensing valve. The mobile sanitizing device may autonomously approach users for sanitization. Various embodiments of the mobile sanitizing device and the operation of the mobile sanitizing device will be described in more detail herein.

Referring now to FIG. 1, one embodiment of a mobile sanitizing device 100 is illustrated. The mobile sanitizing device 100 generally comprises a motorized wheel assembly 130 and a sanitizer solution dispenser module 150 coupled to the motorized wheel assembly 130 via a device body 111. The mobile sanitizing device 100 may be powered by a rechargeable battery pack. A dispensing device 154 is disposed within a housing 152 of the sanitizer solution dispenser module. The dispensing device 154 may be operable to dispense a sanitizer solution, such as a hand sanitizer solution, for example. The illustrated housing 152 is generally spherical in shape and may be made of a lightweight plastic or metal material. It should be understood that embodiments are not limited to the spherical configuration as other shapes may be utilized. The interior of the housing 152 may also maintain other components such as a controller module 160 and balance control sensor 122 that are described in detail below. As illustrated in FIG. 1, the housing 152 may define an opening 153 into which a user may position his or her hands 180 to receive the sanitizer solution during a sanitizing session. In other embodiments, the housing 152 may not define an opening and the dispensing device 154 be externally exposed.

The dispensing device 154 generally comprises a sanitizer solution reservoir 155 that may be filled with a sanitizer solution and a dispensing valve 158 having a nozzle 151. The sanitizer solution reservoir is fluidly coupled to a dispensing valve 158. The dispensing valve 158 may be actuated to dispense a predetermined amount of sanitizer solution through a downward nozzle 151 toward the hands 180 of a user. The dispensing valve 158 may be actuated by a motion sensor (not shown) that detects when hands are present. When the user positions his or her hands into the opening 153, the dispensing valve 158 will activate and provide a predetermined amount of sanitizer solution through the downward nozzle 151.

The sanitizer solution dispenser module 150 may be coupled to a device body 111. The device body 111 may be integral with the sanitizer solution dispenser module 150 as one component (e.g., the device body 111 and the sanitizer solution dispenser module 150 may be molded or formed as one component) or as separate components that are mechanically coupled together by fasteners, for example. In the illustrated embodiment, the device body 111 comprises a lower section 116 that is coupled to the motorized wheel assembly 130 and an upper section 114 that is coupled to the sanitizer solution dispenser module 150. Although the mobile sanitizing device 100 is illustrated as having a two-section device body 111, embodiments are not limited thereto. Embodiments may comprise a device body 111 having a single section, for example. In one embodiment, the upper section 114 may be slidably coupled to the lower section 116 such that a height of the mobile sanitizing device 100 may be adjusted by translating the upper section 114 along the lower section 116. It should be understood that embodiments may not have a device body 111 such that the sanitizer solution dispenser module 150 is coupled directly to the motorized wheel assembly 130 or is coupled by components other than a device body.

The device body 111 may also maintain various electronic components, such as the balance control sensor 122 and the controller module 160. As described in more detail below, the balance control sensor 122 and controller module 160 may cooperate to generate drive signals that are applied to the motorized omni-directional wheel such that the mobile sanitizing device 100 may retain its balance in a substantially vertical orientation, as well as move in various directions.

Figure 2:
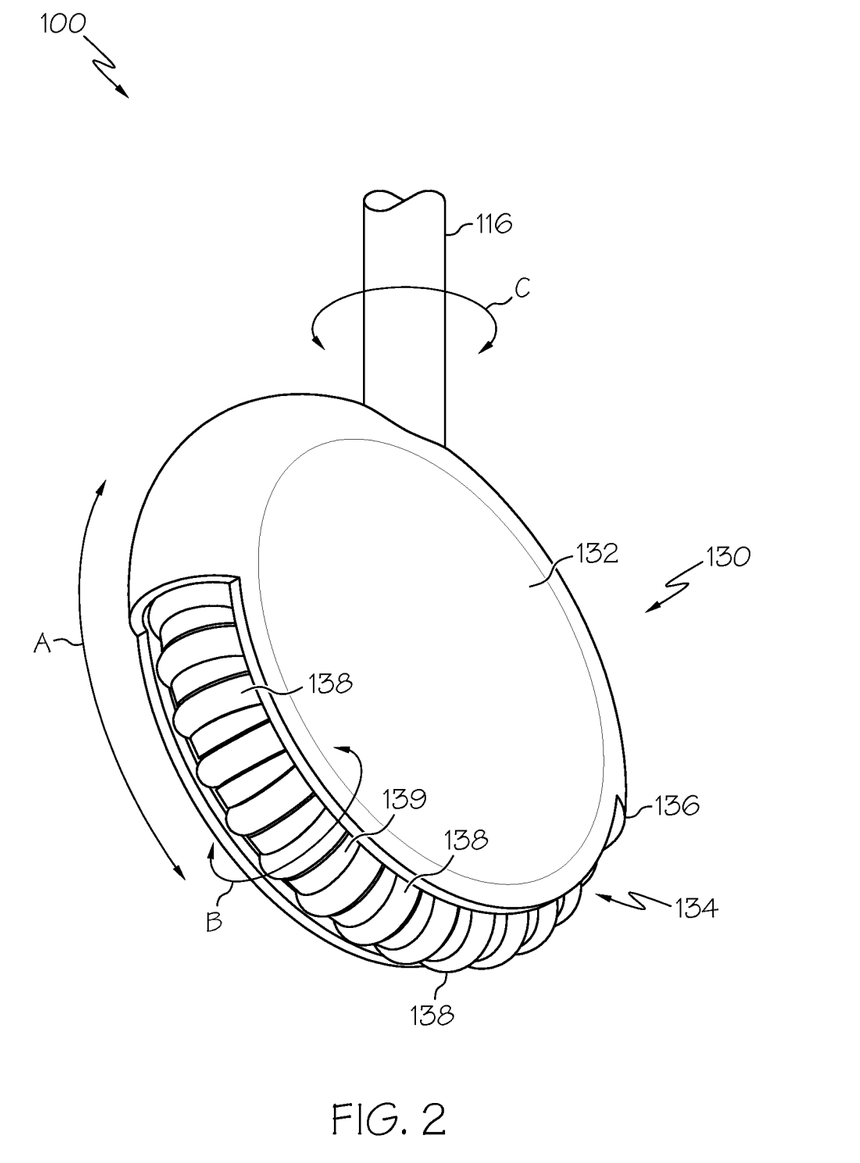
FIG. 2 depicts an omni-directional wheel of a mobile sanitizing device according to one or more embodiments shown and described herein.

FIG. 2 illustrates the motorized wheel assembly 130 comprising the omni-directional wheel 134 depicted in FIG. 1. Although embodiments may be described herein in the context of motorized wheel assemblies having a single omni-directional wheel, embodiments are not limited thereto. The motorized wheel assembly may have any number of wheels that may be used to support the sanitizer solution dispenser module. For example, the mobile sanitizing device may have three or four motorized wheels such that the mobile sanitizing device may remain in an upright position without inverted pendulum control as described below with reference to embodiments having an omni-directional wheel.

The motorized wheel assembly 130 may comprise a motorized omni-directional wheel 134 that is disposed within a wheel housing 132 having an opening 136 through which the omni-directional wheel 134 may contact a supporting surface such as a floor. The wheel housing 132 may be made of a metal material such as stainless steel or aluminum, for example, or a molded plastic material. The wheel housing 132 may be integral with the device body 111 or separate components.

The motorized omni-directional wheel 134 may be configured as a wheel 139 around a circumference of which a plurality of motorized roller elements 138 are positioned. The wheel 139 may be made of metal or a rigid plastic material. Referring to both FIGS. 1 and 2, the wheel 139 may be rotated in an angular direction (depicted by arrow A) by the application of one or more drive signals 163 (see FIGS. 5 and 6) to a drive motor (not shown). The rotation of the wheel 139 in the angular direction A causes the mobile sanitizing device 100 to travel in directions 140 and 142 as shown in FIG. 1.

Each of the plurality of roller elements 138 may be rotated in an angular direction as depicted by arrow B. The roller elements 138 may be individually or cooperatively rotated. The angular direction of rotation of each roller element 138 is perpendicular to the angular direction of rotation of the wheel 139. In one embodiment, each roller element 138 is mechanically coupled to an individual roller element motor (not shown) that may be actuated with the application of a drive signal to initiate rotation of the roller element 138. The rotation of the roller elements 138 may enable the mobile sanitizing device to travel in directions 141 and 143, which are perpendicular to directions 140 and 142 provided by the rotation of the wheel 139. The roller elements may have an exterior portion made of rubber or another similar material that provide increased friction between the omni-directional wheel 134 and the support surface.

As described in more detail below, drive signals 163 may be provided to the motorized wheel assembly 130 such that the rotation of the wheel 139 and roller elements 138 cooperatively rotate to enable the mobile sanitizing device 100 to travel in a plurality of directions while retaining its balance using an inverted balance control. Other omni-directional wheel configurations and controls may also be incorporated into the motorized wheel assembly 130 and embodiments are not limited to the omni-directional wheel illustrated in FIGS. 1-3. In one embodiment, the motorized wheel assembly 130 may be rotatably coupled to the device body 111 such that the wheel 139 may be controllably rotated in a direction as indicated by arrow C in combination with or in lieu of the rotation of roller elements 138 to provide omni-directional functionality. In this embodiment, the motorized wheel assembly 130 may turn in the intended direction of travel.

Figure 3:
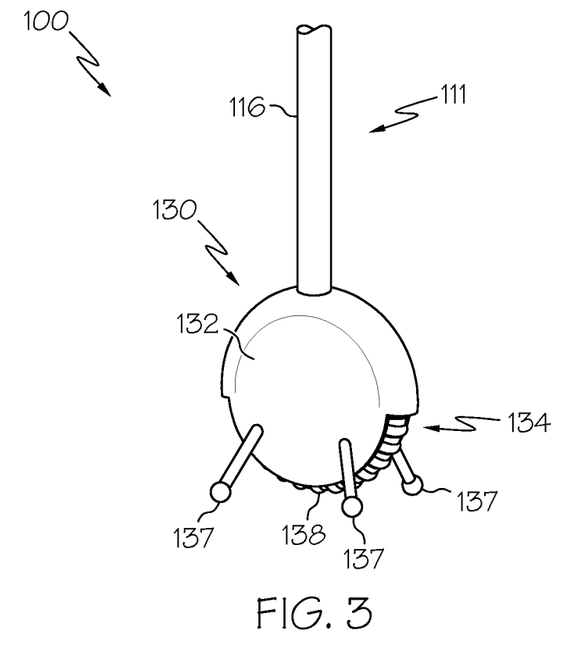
FIG. 3 depicts a mobile sanitizing device in an upright position having retractable auxiliary supports in a deployed position according to one or more embodiments shown and described herein.

Referring to FIG. 3, a mobile sanitizing device 100 is illustrated comprising a motorized wheel assembly 130 having a single motorized omni-directional wheel 134 that further comprises retractable auxiliary supports 137 that aid in maintaining the mobile sanitizing device in a vertical orientation when the mobile sanitizing device is in a power-off mode. The auxiliary supports 137 may include a wheel or stopper that contacts the support surface such that the mobile sanitizing device 100 does not fall over when the inverted pendulum control is inactive or the mobile sanitizing device is not powered on. The auxiliary supports may be maintained within the wheel housing 132 and automatically deployed when the power is turned off or during an emergency situation. In one embodiment, the auxiliary supports 137 may be folded into the wheel housing 132 during operation of the mobile sanitizing device 100 (i.e., an unsupported mode) and then pivot away from the wheel housing 132 toward the support surface when the mobile sanitizing device is powered down (i.e., a supported mode). FIG. 1 illustrates a mobile sanitizing device 100 in which the auxiliary supports are retracted within the wheel housing.

Figure 4:
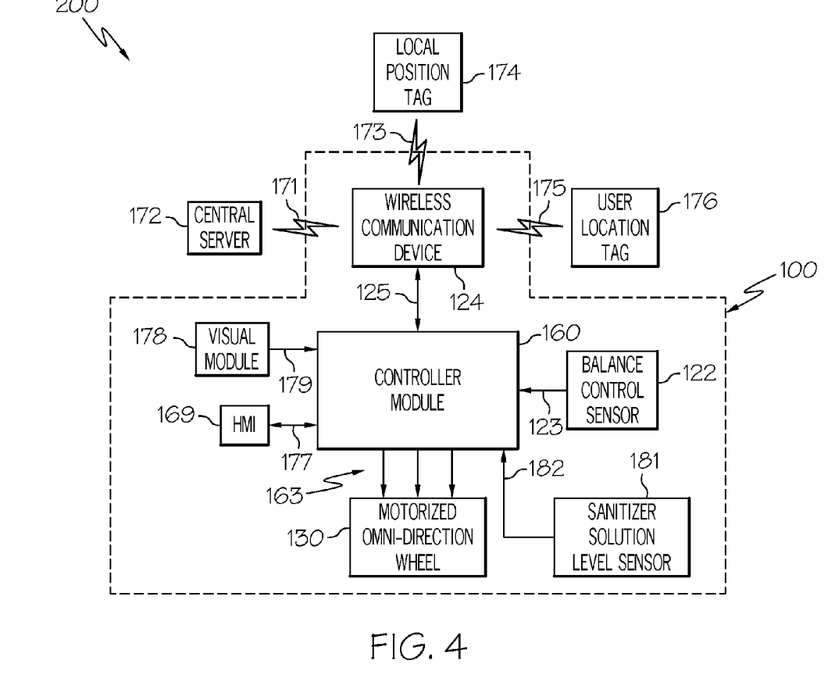
FIG. 4 depicts a block schematic illustration of a sanitization system according to one or more embodiments shown and described herein.
Figure 5:
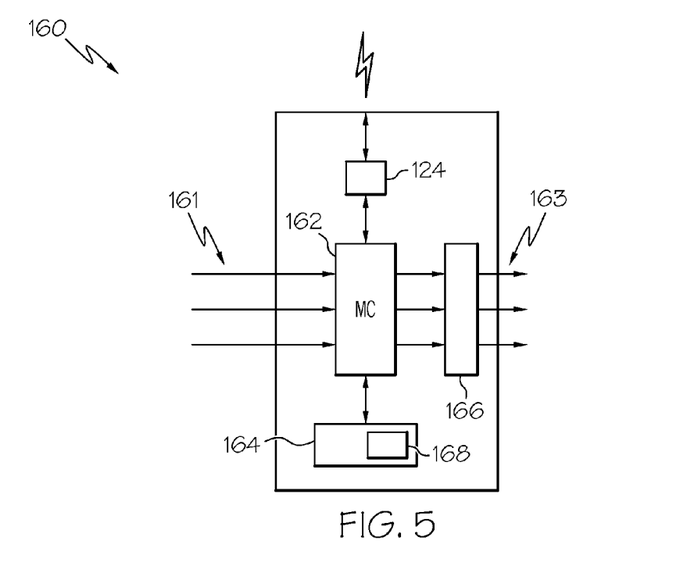
FIG. 5 depicts a block schematic illustration of a controller module of a mobile sanitizing device according to one or more embodiments shown and described herein.

The motorized wheel assembly 130 may be controlled by the application of one or more drive signals produced and provided by a controller module 160. FIG. 4 illustrates a schematic of an exemplary sanitization system, while FIG. 5 illustrates a schematic of an exemplary controller module 160. Referring to both FIGS. 4 and 5, the controller module 160 may comprise a microcontroller 162, memory 164, and drive signal electronics 166. The controller module 160 may include other components not shown, such as input signal conditioning circuits to prepare the input signals 161 prior to being received at the microcontroller 162, an analog to digital converter for converting analog input signals 161 into digital signals, etc. In some embodiments, the microcontroller 162 may comprise integrated analog-to-digital and digital-to-analog converters.

The input signals 161 may include input signals provided by the various sensors. For example, the controller module 160 illustrated in FIG. 4 may receive a balance signal 123 from a balance control sensor 122, a visual signal 179 from a visual module 178, an input signal 177 from a human machine interface (HMI) 169, and proximity and wireless data 125 from a wireless communications device 124. The various input signals are referred to generally as input signals 161 in FIG. 5. The microcontroller 162 receives these input signals 161 to determine how to instruct the motorized wheel assembly 130 to rotate. The memory 164 is operable to store computer readable instructions 168 that, when read and executed by the microcontroller 162, cause the controller module to produce the drive signals 163 that are provided to the motorized wheel assembly 130. In embodiments that utilize a single motorized omni-directional wheel 134, the set of executable instructions 168 may include an inverted pendulum control algorithm that calculates a balancing velocity of the motorized omni-directional wheel that is based on the balance signal 123.

The drive signal electronics 166 may be provided to receive signals from the microcontroller 162 and produce drive signals 163 that are sent to the motorized wheel assembly 130 to control the motion and balance control of the mobile sanitizing device 100. The drive signal electronics 166 may include transistors or other switching devices that are configured to output voltage or current in accordance with instructions from the microcontroller 162. The drive signal or signals 163 provided to motorized wheel assembly 130 may depend on the particular type and configuration of motorized wheel assembly. In another embodiment, the drive control electronics 166 may further comprise digital-to-analog converters operable to translate digital signals provided by the microcontroller 162 into analog signals to produce analog drive signals 163 that are provided to the motorized wheel assembly 130.

Figure 6:
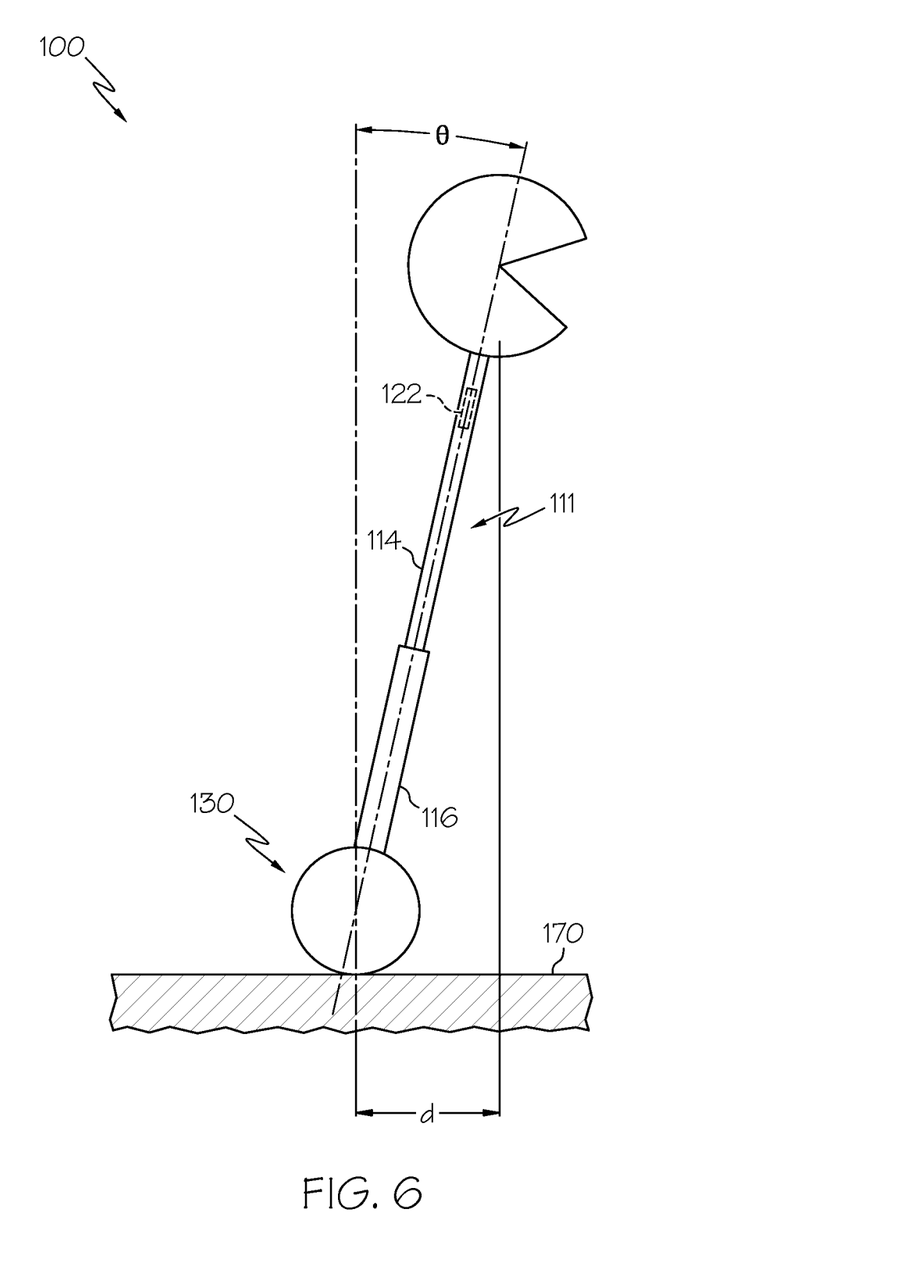
FIG. 6 depicts a side view of a mobile sanitizing device in an angled orientation according to one or more embodiments shown and described herein.

Referring now to FIG. 6, the balance control sensor 122 determines an orientation and movement of the mobile sanitizing device 100. The balance control sensor 122 may comprise one or more gyroscope and/or accelerometer devices that are capable of determining an orientation of the mobile sanitizing device 100 with respect to a vertical orientation, as well as an acceleration of the mobile sanitizing device 100. The balance signal 123 provided by the balance control sensor 122 corresponds to an orientation angle θ between a central axis of the mobile sanitizing device 100 and a vertical orientation, as well as an offset horizontal distance d along the support surface 170 from the central axis of the mobile sanitizing device 100 to the rotational axis of the omni-directional wheel. For example, the balance signal 123 provides information relating to a direction and acceleration in which the mobile sanitizing device may be tipping over.

In embodiments utilizing an omni-directional wheel 134, the controller module 160 may have an inverted pendulum control algorithm stored in the memory 164 to maintain the mobile sanitizing device 100 balanced in a substantially upright position during an autonomous standing operation with no user interaction. During both an autonomous standing operation and a movement operation, the controller module 160 maintains the mobile sanitizing device 100 in a substantially upright position. The inverted pendulum control algorithm may be based on fuzzy control logic, H-infinity methods ("$H_\infty$ control logic"), or any other feedback methodology to calculate a balancing velocity of the omni-directional wheel 134 to keep the mobile sanitizing device 100 in a substantially upright position. In accordance with the inverted pendulum control, the omni-directional wheel rotates to cause the mobile sanitizing device 100 to move slightly to counter a falling motion of the mobile sanitizing device such that mobile sanitizing device remains substantially upright. Still referring to FIG. 6, the illustrated mobile sanitizing device 100 is orientated at a relatively large orientation angle θ. Using fuzzy or $H_\infty$ control logic, the controller module 160 calculates a balance velocity indicative of an angular speed and direction that the omni-directional wheel 134 should be rotated to retain the mobile sanitizing device 100 in an upright position. The drive electronics 166 of the controller module then provides one or more drive signals to the omni-directional wheel 134 so that the wheel rotates accordingly such that the wheel travels a horizontal distance d (i.e., in the right direction), thereby making the orientation angle θ and offset distance d equal to zero. Therefore, the inverted pendulum control algorithm may cause the omni-directional wheel to make continuous corrective rotations to keep the mobile sanitizing device substantially upright without user intervention.

Referring now to FIGS. 1 and 6, the mobile sanitizing device 100 may further comprise a wireless communications device 124 to receive wireless signals from various sources. The wireless communications device 124 may be communicably coupled to a wireless communications network. Generally, the wireless communications device 124 may receive wireless signals that are indicative of a location of the mobile sanitizing device 100 within an area 101 (e.g., an area of a facility such as a hospital, nursing home, rehabilitation facility, zoo, childcare center, laboratory, or any other area where people congregate and diseases may be present), of a location of one or more users within the area 101, and of obstacles within the area 101. The wireless signals may also correspond with navigation data received from a central server 172 as part of a sanitization system 200, which may also be communicably coupled to the wireless communications network (wireless signals 171). The wireless communications device 124 may also transmit wireless signals to the central server 172 and other device to navigate within the area 101.

The mobile sanitizing device 100 may be configured to determine its location within an area 101. In one embodiment, a plurality of local position tags 174 may be located throughout a facility implementing the sanitization system 200 (e.g., a floor or ward of a hospital). The local position tags 174 may be located on walls, obstacles (e.g., desks, nurses stations, chairs, etc.) or other regions. The local position tags 174 may emit a wireless signal 173 that is uniquely addressed. The wireless communications device 124 (and controller module 160) may receive the wireless signals from the local position tags 174 and use such signals to determine a position of the mobile sanitizing device 100 within the facility. The position may then be used to navigate the mobile sanitizing device 100 throughout the facility. The local position tags 174 may define portions of the area 101 that are restricted to prevent the mobile sanitizing device 174 from entering such areas. Infrared and/or ultrasonic sensors may also be used for collision avoidance.

The mobile sanitizing device 100 may also use other methods of determining a location within the facility, such as a global position system, for example.

The mobile sanitizing device 100 is also capable of detecting the location of users within an area 101. Users of the mobile sanitizing device 100 may wear or carry user location tags 176 that emit a uniquely addressed wireless signal 175. The wireless communications device 124 (and controller module 160) may receive the wireless signals from the user location tags 176. The controller module 160 may determine a location of each of the users based on the receipt of the uniquely addressed user location wireless signals 175. As described in more detail below, the controller module 160 may produce and provide drive signals 163 to the motorized wheel assembly 130 such that the mobile sanitizing device 100 navigates throughout the facility to approach users in need of sanitization.

In one embodiment, the wireless communications device 124 collects the location data corresponding to the location of the mobile sanitizing device 100 within the facility as well as the location of the one or more users and then transmits the location data to the central server over the wireless communications network. The central server 172 may then calculate a navigation route based on the location data. Navigation data corresponding to the navigation route may be wirelessly communicated to the wireless communications device 124 and then passed to the controller module 160. The controller module then produces drive signals 163 that cause the motorized wheel assembly 130 to rotate to follow the navigation route. For example, the navigation route may direct the mobile sanitizing device 100 to a particular user in need of hand sanitization. In another embodiment, the controller module 160 may itself use the location data to calculate the navigation route rather than transmitting the location and navigation data over the wireless communications network.

As described in more detail below, the mobile sanitizing device 100 is programmed to autonomously approach users that are in most urgent need of hand sanitization. The need may be determined based on a sanitization record of the particular user, an action taken by a user, or other factors. The mobile sanitizing device 100 may also autonomously approach a user after receiving a sanitization request signal, which may be a remote control signal or a verbal signal spoken by a user. Further, the mobile sanitizing device 100 may be programmed to autonomously approach users that have entered a particular room within the facility, or that have passed by a certain location.

An operation of a mobile sanitizing device 100 will now be described. Referring to FIGS. 1 and 4, a mobile sanitizing device 100 may autonomously approach a user to provide hand sanitization. Based on the detected identity of the user that the device 100 is approaching, the device body 111 may adjust its height so that the overall height of the device is appropriate for the particular user. The user may then place his or her hands 180 into the opening 153 of the sanitizer solution dispenser module 150. In some embodiments, the sanitizer solution dispenser module 150 further comprises a human machine interface (HMI) device in the form of a video screen 169. The video screen 169 may show a hand sanitization instructional video to teach users on proper hand sanitizing techniques. The HMI device may also have menu function buttons that a user may select to verify his or her identity or make preference modifications (e.g., how often he or she wants to sanitize, a height of the user, etc.).

Upon placing his or her hands into the opening, the sanitizer solution dispenser module 150 detects the user's hands and the dispensing valve 158 dispenses sanitizer solution maintained in the sanitizer solution reservoir through the downward nozzle 151. The user the rubs his or her hands together to spread the sanitizer solution completely over his or her hands. In one embodiment, the HMI device comprises a speaker that provides a countdown audio signal that indicates to the user how long he or she should rub his or her hands together. The video screen 169 may also depict a similar countdown. If the user attempts to move away from the mobile sanitizing device 100 before the completion of the countdown, an alert indicating that the sanitization was not completed may be issued (e.g., audibly or visibly). The mobile sanitizing device 100 may also be equipped with a hand dryer that blows warm air onto the user's hands 180 after the completion of the sanitization session.

After the user has successfully sanitized his or her hands, the controller module 160 logs a sanitization record into a sanitization history associated with the particular user. The sanitization record may include the name of the user, the date and time of the sanitization session, and the location in which the sanitization session occurred. The sanitization record and sanitization history may be stored locally in the memory 164 of the controller module 160 and may also be transmitted to the central server 172 via the wireless communications device 124.

The mobile sanitizing device 100 may determine which users are in need of sanitization based on the sanitization history associated with each user. The sanitization history may be compared with a sanitization standard (e.g., an acceptable length of time between sanitization sessions, where a sanitization session is to take place, etc.). The device 100 may then remain close to those in need of hand sanitization. For example, the controller module 160 may organize the users into a queue in which users most in need of sanitization are placed first. The user having not performed sanitization the longest may be at the top of the queue. The device 100 may be programmed to approach users that have not sanitized for a certain period of time. As an example and not a limitation, in a hospital setting the mobile sanitizing device 100 may be programmed to approach target users (e.g., nurses and doctors) that have not performed a sanitizing session for at least one hour.

The mobile sanitizing device 100 may also receive a signal from a user that he or she desires to complete a sanitizing session. For example, the user may call the device 100 by saying a command word. The command word may be particular to the user so that the device 100 may know which user is requesting sanitization and then autonomously approach that user based on the corresponding user location tag 176. The signal may also be a wireless remote control signal.

Figure 7:
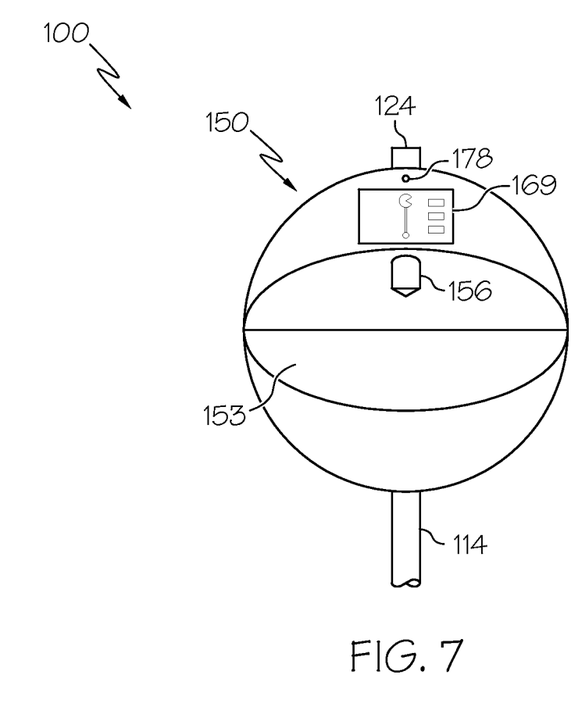
FIG. 7 depicts a front view of a mobile sanitizing device comprising a human machine interface and a visual module according to one or more embodiments shown and described herein.

Referring to FIG. 7, some embodiments of the mobile sanitizing device 100 may also be equipped with a visual module 178 for detecting gestures of users. The visual module 178 may be a camera capable of visually monitoring the users. As an example, a user may make a hand gesture toward the mobile sanitizing device 100 that is indicative of a hand sanitizing request. The mobile sanitizing device 100 may then autonomously approach the user. As another example and not a limitation, one or more mobile sanitizing devices 100 may be deployed in a petting zoo or other areas of a zoo that allow people to physically touch animals. A mobile sanitizing device 100 may use the visual module 178 to determine when a person has physically contacted an animal with his or her hands. The mobile sanitizing device 100 that detects a person who has touched an animal may then approach the user to initiate hand sanitization. Such gesture detection may be utilized in any facility or application and is not limited to zoos.

The mobile sanitizing device 100 may continue to operate until its battery charge becomes below a threshold level, or a level of sanitizer solution within the sanitizer solution reservoir becomes below a threshold level. The sanitizer solution level may be monitored by a sanitizer solution level sensor 181 that produces a corresponding sanitizer solution level signal 182. If the battery charge or sanitizer solution levels drop below the respective threshold levels, the mobile sanitizing device 100 may autonomously return to a battery recharge and/or sanitizer refill location where the battery may be recharged and the sanitizer solution reservoir may be refilled with sanitizer solution.

A sanitization system 200 may comprise a plurality of deployed mobile sanitizing devices 100 that may communicate with one another over the wireless communications network. The mobile sanitizing devices 100 may be deployed according to zone coverage such that the devices may equally cover an overall area 101. The zones may be delineated by local position tags 174 such that each mobile sanitizing device 100 stays within its respective zone. Alternatively, the devices 100 may stay in their respective zones based on navigation data received from the central server 172. In another embodiment, each deployed mobile sanitizing device 100 may be programmed to cover particular users so that the mobile sanitizing devices have equal coverage of all of the users within the facility or area of the facility.

It should now be understood that the embodiments of the mobile sanitizing devices described herein may be used to provide sanitization to users throughout a facility. The mobile sanitizing devices may autonomously approach users that are in need of hand sanitization in accordance with a sanitization history, a sanitization request signal, or gesture recognition. Some embodiments of the mobile sanitizing device may comprise a single omni-directional wheel to minimize the amount of space taken up by the device.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A mobile sanitizing device for dispensing sanitizer solution comprising:
   a sanitizer solution dispenser module operable to dispense the sanitizer solution;
   a motorized wheel assembly comprising at least one wheel, wherein the motorized wheel assembly is coupled to the sanitizer solution dispenser module; and
   a controller module comprising a microcontroller and a memory, wherein the controller module:
      logs a sanitization record into a sanitization history for at least one user, wherein the sanitization history is stored in the memory;
      compares the sanitization history of the user with a sanitization standard; and
      controls the mobile sanitizing device to approach the user to dispense sanitizing solution to the user when the sanitization history does not meet the sanitization standard.

2. The mobile sanitizing device of claim 1 further comprising a wireless communications device, wherein:
   the wireless communications device receives a wireless signal from one or more user location tags associated with the user, the wireless signal indicative of a location of the mobile sanitizing device and a location of the user within a facility, and the wireless communications device provides proximity data to the controller module; and
   the controller module provides a drive signal to the motorized wheel assembly in accordance with the proximity data to cause the mobile sanitizing device to approach the user.

3. The mobile sanitizing device of claim 1 wherein each sanitization record comprises a user name, a date and time of a sanitization session, and a sanitization location.

4. The mobile sanitizing device of claim 1 wherein:
   the mobile sanitizing device further comprises a visual module electrically coupled to the controller module for visually capturing an action of the user; and
   the controller module causes the mobile sanitizing device to approach the user if the action of the user captured by the visual module corresponds to a sanitizing action.

5. The mobile sanitizing device of claim 1 wherein the controller module receives a sanitization request signal and causes the mobile sanitizing device to approach a user in accordance with the sanitization request signal.

6. The mobile sanitizing device of claim 1 wherein the controller module causes the mobile sanitizing device to remain in closer proximity to users having a greater need of sanitization in accordance with corresponding sanitization histories than users having a lesser need of sanitization in accordance with the corresponding sanitization histories.

7. The mobile sanitizing device of claim 1 wherein:
   the sanitizer solution dispenser module further comprises a sanitizer solution level sensor that provides a sanitizer solution level signal to the controller module; and
   the controller module causes the mobile sanitizing device to navigate to a sanitizer refill location.

8. The mobile sanitizing device of claim 1 wherein the motorized wheel assembly comprises an omni-directional wheel.

9. A mobile sanitizing device for dispensing a sanitizer solution comprising:
 a sanitizer solution dispenser module operable to dispense the sanitizer solution;
 a motorized wheel assembly comprising an omni-directional wheel, wherein the motorized wheel assembly is coupled to the sanitizer solution dispenser module;
 a balance control sensor, wherein the balance control sensor provides a balance signal corresponding to an orientation of the mobile sanitizing device; and
 a controller module comprising a microcontroller and a memory, wherein the controller module receives the balance signal from the balance control sensor and provides a drive signal to the motorized wheel assembly in accordance with the balance signal and an inverted pendulum control algorithm such that the mobile sanitizing device remains in an upright position when the mobile sanitizing device is operated in an unsupported mode.

10. The mobile sanitizing device of claim 9 wherein the inverted pendulum control algorithm comprises fuzzy control logic or H-infinity control logic.

11. The mobile sanitizing device of claim 9 further comprising a plurality of retractable auxiliary supports coupled to the motorized wheel assembly, wherein the auxiliary supports are in an engaged position when the mobile sanitizing device is operated in a supported mode such that the auxiliary supports engage a supporting surface, and the auxiliary supports are in an unengaged position when the mobile sanitizing device is operated in an unsupported mode such that the auxiliary supports are disengaged from the supporting surface.

12. The mobile sanitizing device of claim 9 wherein the controller module:
 logs a sanitization record into a sanitization history of at least one user, wherein the sanitization history is stored in the memory;
 compares the sanitization history of the user with a sanitization standard; and
 provides a drive signal to the motorized wheel assembly to cause the mobile sanitizing device to approach a user in accordance with at least the sanitization history of the user and the sanitization standard.

13. The mobile sanitizing device of claim 9 further comprising a wireless communications device, wherein:
 the wireless communications device receives a wireless signal from one or more user location tags associated with the user, the wireless signal indicative of a location of the mobile sanitizing device and a location of the user within a facility, and the wireless communications device provides proximity data to the controller module; and
 the controller module provides a drive signal to the motorized wheel assembly in accordance with the proximity data to cause the mobile sanitizing device to approach the user.

14. The mobile sanitizing device of claim 9 wherein the controller module receives a sanitization request signal and causes the mobile sanitizing device to approach a user in accordance with the sanitization request signal.

15. The mobile sanitizing device of claim 9 wherein the controller module causes the mobile sanitizing device to remain in closer proximity to users having a greater need of sanitization in accordance with corresponding sanitization histories than users having a lesser need of sanitization in accordance with the corresponding sanitization histories.

16. A sanitization system comprising:
 a wireless communications network;
 a central server communicably coupled to the wireless communications network; and
 a mobile sanitizing device comprising:
  a sanitizer solution dispenser module operable to dispense a sanitizer solution;
  a motorized wheel assembly comprising at least one wheel, wherein the motorized wheel assembly is coupled to the sanitizer solution dispenser module; and
  a controller module comprising a microcontroller, a memory, and a wireless communications device communicably coupled to the wireless communications network, wherein:
   the wireless communications device receives a wireless signal indicative of a location of the mobile sanitizing device and a location of a user, and transmits proximity data over the wireless communications network;
   the central server receives the proximity data over the wireless communications network, calculates a navigation route, and transmits navigation information to the wireless communications device over the wireless communications network in accordance with the navigation route; and
   the controller module receives the navigation information from the central server and provides a drive signal to the motorized wheel assembly to cause the mobile sanitizing device to autonomously approach a user to dispense the sanitizer solution to the user.

17. The sanitization system of claim 16 further comprising:
 a plurality of user location tags, wherein each user location tag transmits a uniquely addressed wireless signal over the wireless communications network and is configured to be associated with a user; and
 a plurality of local position tags, wherein each local position tag transmits a uniquely addressed wireless signal over the wireless communications network.

18. The sanitization system of claim 17 wherein the wireless signal is received from one or more user location tags.

19. The sanitization system of claim 17 wherein at least one said mobile sanitizing device is deployed in an area.

20. The sanitization system of claim 16 wherein:
 the controller module is programmed to:
  log a sanitization record into a sanitization history of at least one user, wherein the sanitization history is stored in the memory;
  compare the sanitization history of the user with a sanitization standard; and
  determine that a user is in need of sanitization if the sanitization history of the user deviates from the sanitization standard; and
 the wireless communications device transmits the sanitization record to the central server.

* * * * *